(12) United States Patent
Sauceda et al.

(10) Patent No.: US 12,239,243 B2
(45) Date of Patent: Mar. 4, 2025

(54) NURSING PILLOW

(71) Applicant: FRIDABABY, LLC, Miami, FL (US)

(72) Inventors: Samuel Sauceda, El Serino, CA (US); Maria Level, Miami, FL (US); Chelsea Hirschhorn, Miami, FL (US)

(73) Assignee: FRIDABABY, LLC, Miami, FL (US)

( * ) Notice: Subject to any disclaimer, the term of this patent is extended or adjusted under 35 U.S.C. 154(b) by 518 days.

(21) Appl. No.: 17/543,115

(22) Filed: Dec. 6, 2021

(65) Prior Publication Data

US 2023/0172370 A1 Jun. 8, 2023

(51) Int. Cl.
*A47D 13/08* (2006.01)
*A61F 7/02* (2006.01)

(52) U.S. Cl.
CPC .............. *A47D 13/083* (2013.01); *A61F 7/02* (2013.01); *A61F 2007/023* (2013.01)

(58) Field of Classification Search
CPC ...... A47G 9/10; A47G 9/1036; A47G 9/1063; A47G 9/1081; A47G 9/109; A47G 2009/1018; A47D 13/083; A61F 7/02; A61F 2007/023
See application file for complete search history.

(56) References Cited

U.S. PATENT DOCUMENTS

| | | | |
|---|---|---|---|
| 4,887,326 A * | 12/1989 | O'Brien | A61F 7/02 5/490 |
| 4,916,765 A * | 4/1990 | Castronovo, Jr. | A47G 9/1081 5/636 |
| 5,029,351 A * | 7/1991 | Weber | A47D 13/083 5/655 |
| 5,092,005 A | 3/1992 | Byrn | |
| 5,261,134 A | 11/1993 | Matthews | |
| 5,301,908 A | 4/1994 | Reames | |
| 5,519,906 A | 5/1996 | Fanto-Chan | |
| 5,661,861 A | 9/1997 | Matthews | |
| 5,790,999 A | 8/1998 | Clark | |
| 6,038,720 A | 3/2000 | Matthews et al. | |
| 6,061,854 A | 5/2000 | Crowley | |
| 6,233,767 B1 | 5/2001 | Horowitz | |
| 6,279,185 B1 | 8/2001 | Matthews | |
| 6,321,403 B1 | 11/2001 | Matthews | |
| 6,412,128 B1 | 7/2002 | Matthews | |
| 6,453,493 B1 | 9/2002 | Matthews Brown | |
| 6,484,337 B1 | 11/2002 | Moe et al. | |
| 6,499,164 B1 | 12/2002 | Leach | |
| 6,553,590 B1 | 4/2003 | Leach | |
| 6,564,408 B2 | 5/2003 | Van Vuuren | |
| 6,625,828 B2 | 9/2003 | Matthews Brown | |
| 6,651,282 B1 | 11/2003 | Skoug et al. | |
| 6,658,681 B2 | 12/2003 | Britto et al. | |
| 6,711,770 B1 | 3/2004 | Owens et al. | |
| 6,779,211 B1 | 8/2004 | Williams | |

(Continued)

FOREIGN PATENT DOCUMENTS

CA 2398394 C 3/2002

*Primary Examiner* — George Sun
(74) *Attorney, Agent, or Firm* — Seyfarth Shaw LLP

(57) ABSTRACT

A nursing pillow has three cushionable inserts of at least two different firmnesses. The user may install or remove any of the inserts through an opening in the outer shell of the pillow. A thermal therapy pocket is joined to an inner panel of the outer shell of the pillow, and is oriented vertically so as to face the torso of the mother.

11 Claims, 17 Drawing Sheets

(56) References Cited

U.S. PATENT DOCUMENTS

| | | | |
|---|---|---|---|
| 6,842,925 B1 | 1/2005 | Owens et al. | |
| 6,851,143 B2 | 2/2005 | Matthews Brown | |
| 7,000,274 B2 | 2/2006 | Matthews Brown et al. | |
| 7,010,821 B1* | 3/2006 | Leach | A47D 13/083 5/636 |
| 7,055,196 B2 | 6/2006 | Littlehorn | |
| 7,089,639 B2 | 8/2006 | Matthews Brown et al. | |
| 7,146,663 B2 | 12/2006 | Brown et al. | |
| 7,404,222 B2 | 7/2008 | Tidwell | |
| 7,430,774 B2 | 10/2008 | Littlehorn et al. | |
| 7,464,423 B2 | 12/2008 | Goodwin et al. | |
| 7,472,443 B2 | 1/2009 | Littlehorn et al. | |
| 7,562,406 B1 | 7/2009 | Leach | |
| 7,703,159 B2 | 4/2010 | Parrilla | |
| 7,788,752 B2* | 9/2010 | Tidwell | A47G 9/10 5/655 |
| 7,810,191 B2 | 10/2010 | Littlehorn et al. | |
| 7,832,036 B2 | 11/2010 | Littlehorn et al. | |
| 7,900,303 B2 | 3/2011 | Mastrosimone-Gese | |
| 8,166,587 B2 | 5/2012 | Collins | |
| 8,205,284 B2 | 6/2012 | Mastrosimone-Gese | |
| 8,418,295 B2 | 4/2013 | Clark | |
| 8,516,638 B2 | 8/2013 | Kummerfeld et al. | |
| 8,590,078 B1 | 11/2013 | Zenoff | |
| 8,595,872 B2 | 12/2013 | Tidwell | |
| D699,981 S | 2/2014 | Kummerfeld et al. | |
| D699,982 S | 2/2014 | Fair et al. | |
| 8,671,480 B1 | 3/2014 | Leach | |
| D704,963 S | 5/2014 | Mcneil et al. | |
| 8,719,982 B2 | 5/2014 | Kelly | |
| 8,950,029 B2 | 2/2015 | Tidwell | |
| 9,113,719 B2* | 8/2015 | Kummerfeld | A47D 13/00 |
| 9,138,072 B1* | 9/2015 | Sanders | A47G 9/0253 |
| 9,167,912 B2* | 10/2015 | Riddick | A47D 13/083 |
| 9,232,863 B1* | 1/2016 | Zenoff | A47D 13/083 |
| 9,265,357 B2 | 2/2016 | Fang | |
| 9,307,842 B2* | 4/2016 | Gibbons | A47C 20/021 |
| 9,532,657 B2 | 1/2017 | Sclare et al. | |
| 9,687,084 B2 | 6/2017 | Sclare et al. | |
| 9,877,597 B2 | 1/2018 | Sclare et al. | |
| 9,936,820 B2 | 4/2018 | Sclare et al. | |
| 2002/0023301 A1* | 2/2002 | Vuuren | A47D 5/00 5/655 |
| 2006/0042012 A1* | 3/2006 | Littlehorn | A47C 20/021 5/632 |
| 2006/0179575 A1* | 8/2006 | Goodwin | A47D 13/083 5/655 |
| 2007/0271703 A1* | 11/2007 | Matthews Brown | A47D 13/08 5/636 |
| 2013/0145556 A1* | 6/2013 | Kummerfeld | A47D 13/083 5/655 |
| 2014/0090169 A1* | 4/2014 | Sclare | A47D 13/083 141/10 |
| 2014/0283303 A1* | 9/2014 | Rochlin | A47G 9/10 5/636 |
| 2015/0101125 A1* | 4/2015 | Fang | A47D 13/08 5/655 |
| 2019/0099289 A1* | 4/2019 | Beck | A61J 13/00 |
| 2019/0231100 A1* | 8/2019 | Pietracatella | A47C 7/383 |
| 2019/0298088 A1* | 10/2019 | Li | A47G 9/10 |
| 2020/0288877 A1* | 9/2020 | Duong | A47C 7/425 |
| 2021/0235885 A1* | 8/2021 | Gibbons | A47D 13/083 |

\* cited by examiner

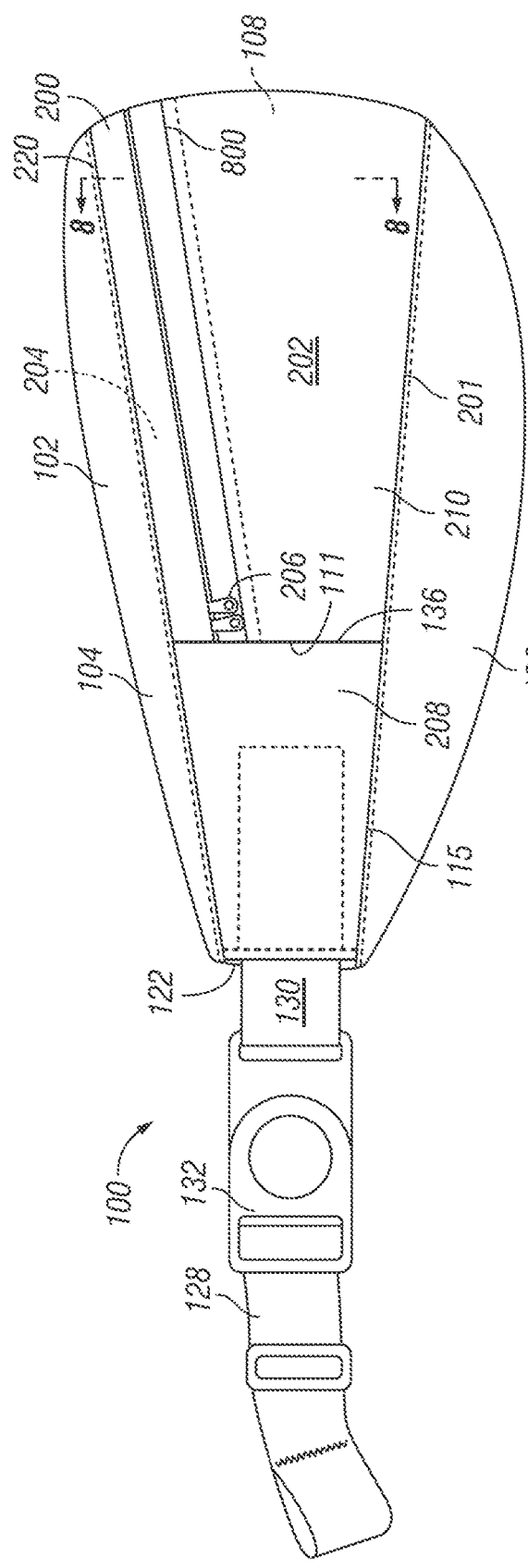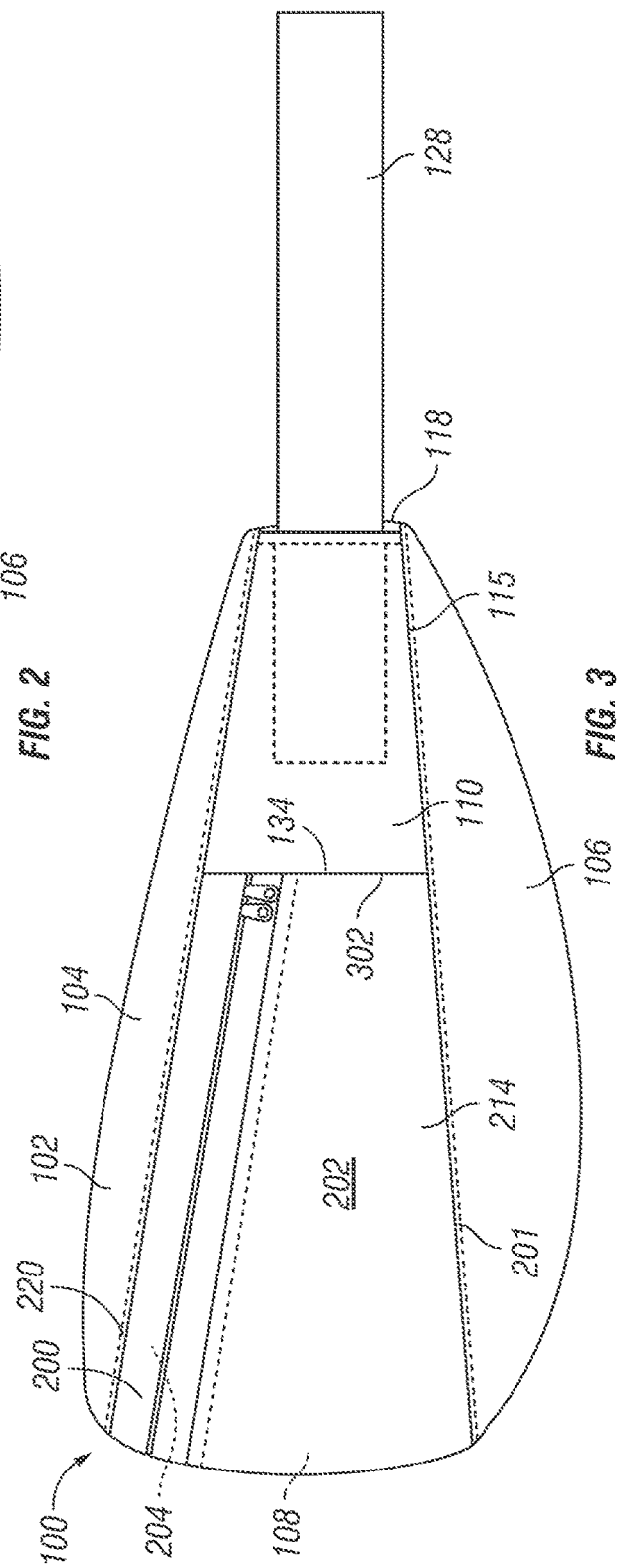
FIG. 2
FIG. 3

NURSING PILLOW

BACKGROUND OF THE INVENTION

Nursing pillows are known in the art. Typical and conventional nursing pillows are shaped or crescent-shaped, so as to fit around the torso of the mother. The nursing pillow is placed on the nursing mother's lap below her breasts. A nursing infant is supported on the upper surface of the pillow. Often, a strap or other connection means is passed around the mother's back, so as to attach a left arm or wing of the pillow to the right arm or wing.

Many nursing pillows have a flexible fabric shell and one or more cushionable inserts for insertion into the shell. U.S. Pat. No. 7,703,159 to Parrilla discloses a nursing platform constructed of foam elements having two different consistencies. U.S. Pat. No. 9,113,719 discloses a nursing pillow in which a stiffening gayer is disclosed to be stiffer than a fill material, U.S. Pat. No. 9,138,072 to Sanders discloses the use of up to four foam inserts for an adjustment of pillow height. Further improvements in the provision, selection and arrangement of cushion inserts of different firmnesses could be made.

Many prior art nursing pillows have been disclosed that have pockets for accessories, and other nursing pillows have provided pockets for items of therapeutic benefit for the infant, e.g., Matthews-Brown U.S. Pat. No. 7,000,274 and Sclare U.S. Pat. No. 9,532,657. None has disclosed a pocket meant to accept a device of therapeutic benefit to the mother.

SUMMARY OF THE INVENTION

According to one aspect of the invention, a nursing pillow is provided that has a flexible outer shell surrounding a pillow body. The outer shell has an opening to a cavity in the pillow body. The body has a middle portion outwardly extending from an inner face that is adapted to be disposed adjacent a front of a torso of a user, a left arm extending leftward from the middle portion and adapted to be disposed adjacent a left side of the torso of the user, and a right arm extending rightward from the middle portion and adapted to be disposed adjacent a right side of the torso of the user.

The nursing pillow further includes a plurality of inserts each capable of being inserted through the outer shell opening so as to be disposed in the cavity. As so inserted, each of the inserts extends into the middle portion, the legit arm and the right arm of the body. The inserts include first, second and third inserts, with the second and third inserts having a firmness greater than the firmness of the first insert. The user may select one or more of the inserts to be disposed inside the cavity. Where plural inserts are selected, each insert is disposed above or underneath the other selected insert(s) so as to be arranged in layers.

In one embodiment, a first insert, having a first firmness, is adapted to be disposed adjacent to the legs of the user. A third insert, having a third firmness greater than a first firmness of the first insert and greater than or equal to a second firmness of the second insert, is adapted to be disposed adjacent to the top surface of the outer shell. In one embodiment, an elongate depression is formed in a top surface of the third insert for receiving a body of a nursing infant. In one embodiment, this elongate depression is bean-shaped such that a front boundary thereof is shorter in distance than a rear boundary thereof.

In one embodiment, the second insert has a similar depression in its top surface, in an addition to or in the place of the depression in the top surface of the third Insert. In one embodiment, the third insert additionally has a bump on its lower surface that fits into the depression made in the top surface of the second insert, when the third insert is stacked on top of the second insert.

According to another aspect of the invention, a nursing pillow is provided with a flexible outer shell. The shell encloses a body with a cavity therein. The body has a middle portion outwardly extending from an inner face adapted to be disposed adjacent a front of a torso of a user, a left arm extending leftward from the middle portion and adapted to be disposed adjacent a left side of the torso of the user, and a right arm extending rightward from the middle portion and adapted to be disposed adjacent a right side of the torso of the user. The nursing pillow further includes a plurality of inserts disposed in the cavity, the plurality including first, second and third inserts, each extending to the middle portion, the left arm and the right arm of the body.

The first insert has a predetermined first firmness and is disposed adjacent the bottom surface of the body. The second insert has a second firmness that is greater (more firm) than the first firmness. The second insert is disposed on top of the first insert. The third insert has a third firmness that is greater than or equal to the second firmness. The third insert is disposed on top of the second insert and to be adjacent the top surface of the body.

In one embodiment, the outer shell includes a top panel forming the top surface of the body, a bottom panel forming the bottom surface of the body, and an outer panel joining the bottom panel to the top panel. The outer panel is disposed remotely from the user. An opening may be formed near the junction of the top and outer panels, such that the user may remove any or all of the first, second and third inserts.

In another aspect of the invention, a nursing pillow is provided which has a flexible outer shell enclosing the body. The body has a cavity therein. The outer shell includes a bottom panel defining a bottom surface of the body, a top panel defining a top surface of the body, and an inner panel joining the top panel to the bottom panel. The inner panel has a substantially vertical surface and is adapted to be disposed adjacent to the user. At least one insert is disposed in the cavity and is resiliently yieldable in response to a downward force (such as the weight of an infant) placed on the top surface of the body. A thermal therapy pocket is joined to the inner panel, so as to be substantially vertically disposed and to face the torso of the user. The thermal therapy pocket is adapted to receive therein a heat or cold therapy device. In one embodiment, the thermal therapy pocket is disposed within the cavity. In another embodiment, the thermal therapy pocket is disposed outside the cavity and frontward from the inner panel.

In one embodiment, the nursing pillow is provided with a strap that is passed around the back of the user to connect together the pillow arms. The strap may pass through a back pad that has a further thermal therapy pocket. In one embodiment, the nursing pillow is provided to the user as including two heat therapy devices, which the user may insert in one or both of the thermal therapy pockets.

In one embodiment, the body has a middle portion extending outwardly from the inner panel, a left arm extending leftwardly around the torso of the user from the middle section, and a right arm extending right Inwardly around the torso of the user from the middle section. Each of the left and right arms has a tip. A left end of the front pawl is disposed leftward of the tip of the left arm, while a right end of the front panel is disposed rightward of the tip of the right arm. The inner panel is formed from a stretchable material. In one embodiment, certain of the remaining panels making up the outer shell have a stretchability that is smaller than that of the front panel, and this may be effected by adding a nonstretch backing or interfacing to the remaining panels' interior surfaces. For example, a nonstretch lining may be provided for the top and outer panels. This helps retain the shape of the nursing pillow.

The nursing pillow of the invention thus is adjustable for infants and nursing mothers of different sizes. One technical advantage of this nursing pillow is its ability to deliver thermal therapy to a nursing mother who may be recovering from childbirth, and/or who may be experiencing uterine contractions, pain from a Caesarian section or back pain.

BRIEF DESCRIPTION OF THE DRAWINGS

Further aspects of the invention and their advantages can be discerned in the following detailed description as read in conjunction with the drawings of exemplary embodiments, in which like characters denote like parts and in which:

FIG. 2 is a right elevational view of the nursing pillow shown in either FIG. 1 or FIG. 1A;

FIG. 3 is a left elevational view of the nursing pillow shown in either FIG. 1 or FIG. 1A;

DETAILED DESCRIPTION

Figure 1:
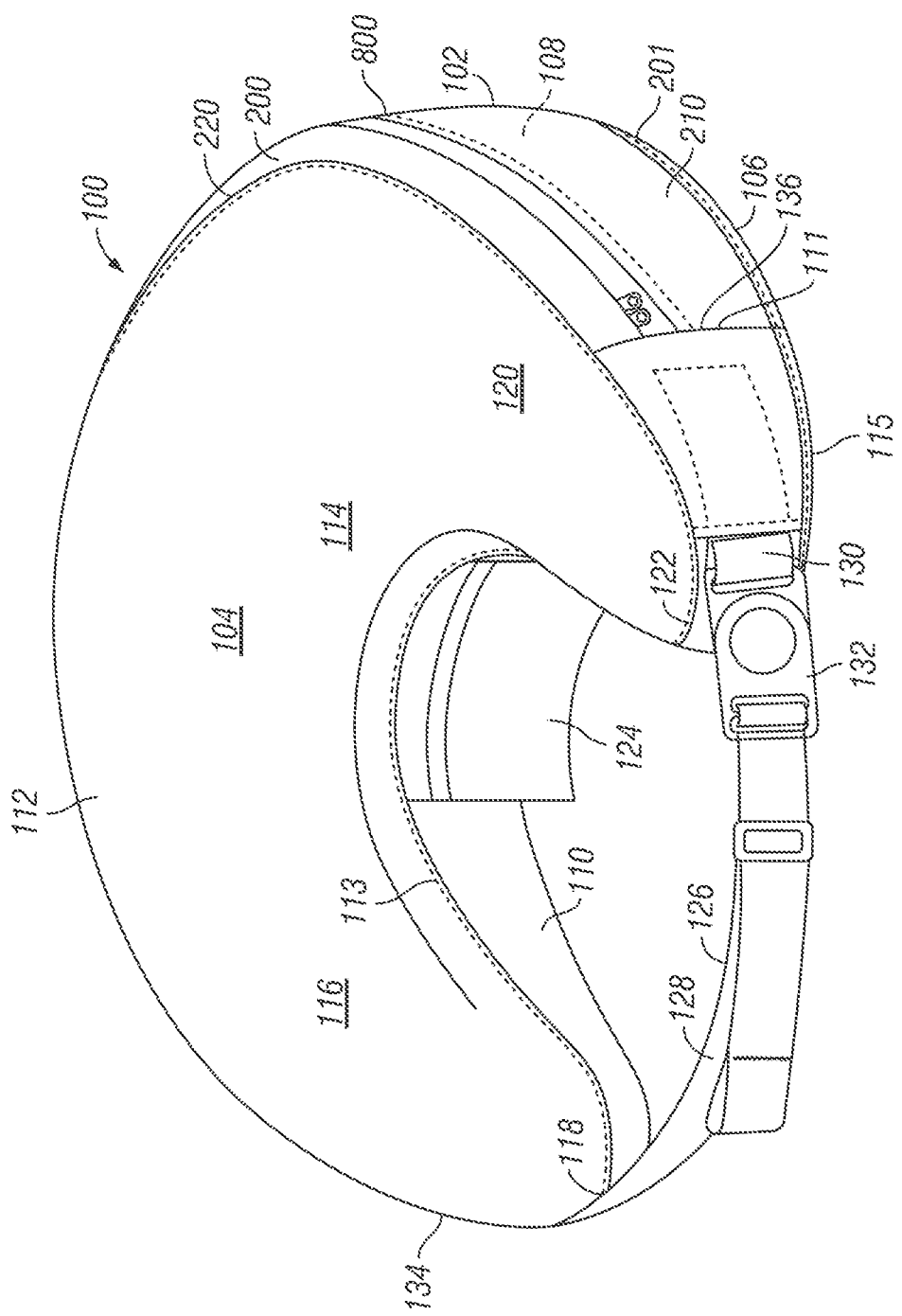
FIG. 1 is a top right perspective view of a nursing pillow according to one embodiment of the invention.

A nursing pillow according to the invention is indicated generally at 100 in FIG. 1. The nursing pillow 100 is encased by a flexible outer shell 102, which preferably is formed by one or more layers of fabric. In one embodiment, the nursing pillow 100 is crescent-shaped and is adapted to fit around the torso of the mother or other user. Shell 102 may be constructed of a top panel 104, a bottom panel 106, an outer or dorsal panel 108, and an inner or ventral panel 110. The inner panel 110 is adapted to be disposed adjacent the front of the torso of the user. The outer panel 108 is then situated to be remote from the user. A left end 134 of the inner panel 110 is connected to a left end of the outer panel 108 by a seam or other junction 302 (FIG. 3). A right end 136 of the inner panel 110 is connected to a right end of the outer panel 108 by a seam or other junction 111. These panels preferably are connected together by stitching, and in the illustrated embodiments, all components of outer shell 102 are connected together likewise.

Each of the inner panel 110 and the outer panel 108 vertically extends from the top panel 104 to the bottom panel 106. Top panel 104 is connected to inner panel 110 by a seam 113. Inner panel 110 is connected to the bottom panel 106 by a seam 115. Outer panel 108 is connected to the bottom panel 106 by a seam 201 (FIGS. 2 and 3).

In the illustrated embodiment, all of the panels 104-110, 208, 300 of outer shell 102 have an outer layer made of a stretchable material such as stretch cotton/rayon. The outer layer may be formed, for example, by a fabric composed of 90% polyester/10% spandex. In addition, panels 104 and 108 are backed with a nonstretch fabric layer 801, 803 that is positioned inwardly of the outer layer. See FIGS. 6, 14A and 14B. This makes panels 104 and 108 less stretchable than inner panel 110 or bottom panel 106. The stretchability of panels 104 and 106 may be so reduced that they are not stretchable at all, and/or are sufficient to ensure that the dimension of either of the backed panels does not substantially change when placed under tension. The nonstretch backing of panels 104, 108 assures that the overall shape of nursing pillow 100 does not change. The inner panel 110, on the other hand, should be remain sufficiently elastic that the arms 116, 120 can be separated so that the pillow 100 can be placed around the mother or other user, and the relative stretchability of the bottom panel 106 means that it will better conform to the legs of the user.

The present invention is principally directed to apparatus to assist nursing mothers and breast-feeding infants, but its utility is not restricted to this situation. The nursing pillow also has application for holding an infant while being fed formula from a bottle, and wherein the caregiver is other than a lactating mother. Hence, the term "user" is used in several instances in this Specification, which should be interpreted to include, but not be limited to, nursing mothers.

The outer shell 102 encloses and defines a pillow body 112. The pillow body 112 has a middle section 114 that outwardly extends from inner panel 110. A left arm 116 extends leftwardly from middle section 114 and terminates in a left tip or end 118. A right arm 120 extends rightwardly from the middle section 114 and terminates in a right tip or end 122. In use, the left arm 116 is adjacent the left side of the user's torso, and the right arm 120 is adjacent the right side of the user's torso.

The middle section 114 is vertically thicker, and horizontally deeper (in a radial direction away from the user), than is either left arm 116 or right arm 120. In the illustrated embodiment, the change in thickness and depth as one proceeds around the torso of the user is continuous, creating a curved crescent shape as shown. The thickness of the inner panel 110 may vary from about 9 cm at its middle, to about 4.5 cm at either end. Its length, when placed flat and prior to assembly into pillow 100, may be about 55-57 cm. A width of the middle section 114, taken on a radius across top panel 104 between inner panel 110 and outer panel 108, can be about 22 cm. A greatest diameter of the nursing pillow, taken from one side of outer panel 108 to an opposite side of outer panel 108, can be about 55 cm.

Figure 15:
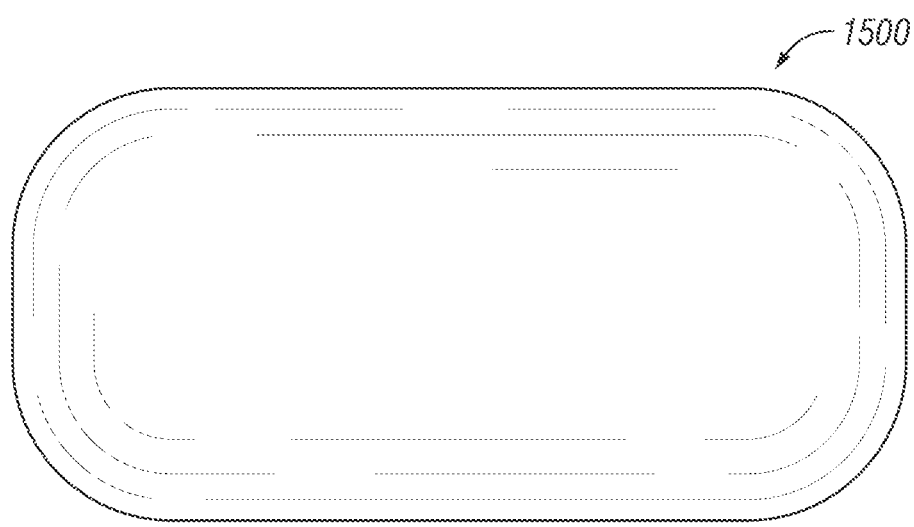
FIG. 15 is an elevational view of a thermal therapy pack for use with the invention.

In one embodiment, a thermal therapy pocket 124 is joined to the inner panel 110 so as to be vertically disposed on the ventral or user-facing face of the inner panel 110. The thermal therapy pocket 124 may receive, for example, a heat pack or a cold pack. A representative sample of such a heat pack or cold pack is shown at 1500 in FIG. 15. As so disposed, the contents of the thermal therapy pocket 124 are optimally arranged to deliver coolness or warmth to the mother or other caregiver. For nursing mothers who have just given birth, a heat therapy pack may be particularly desirable, as a treatment for postpartum uterine contractions or c-section incision soreness. The invention therefore acts as an aid to the overall comfort of a new nursing mother. Further details of the thermal therapy pocket 124 will be described below. In one embodiment the heat therapy pack 1500 is a heat pack containing a substance that changes state between solid crystals and liquid, releasing energy to the mother as the liquid crystallizes.

Figure 1A:
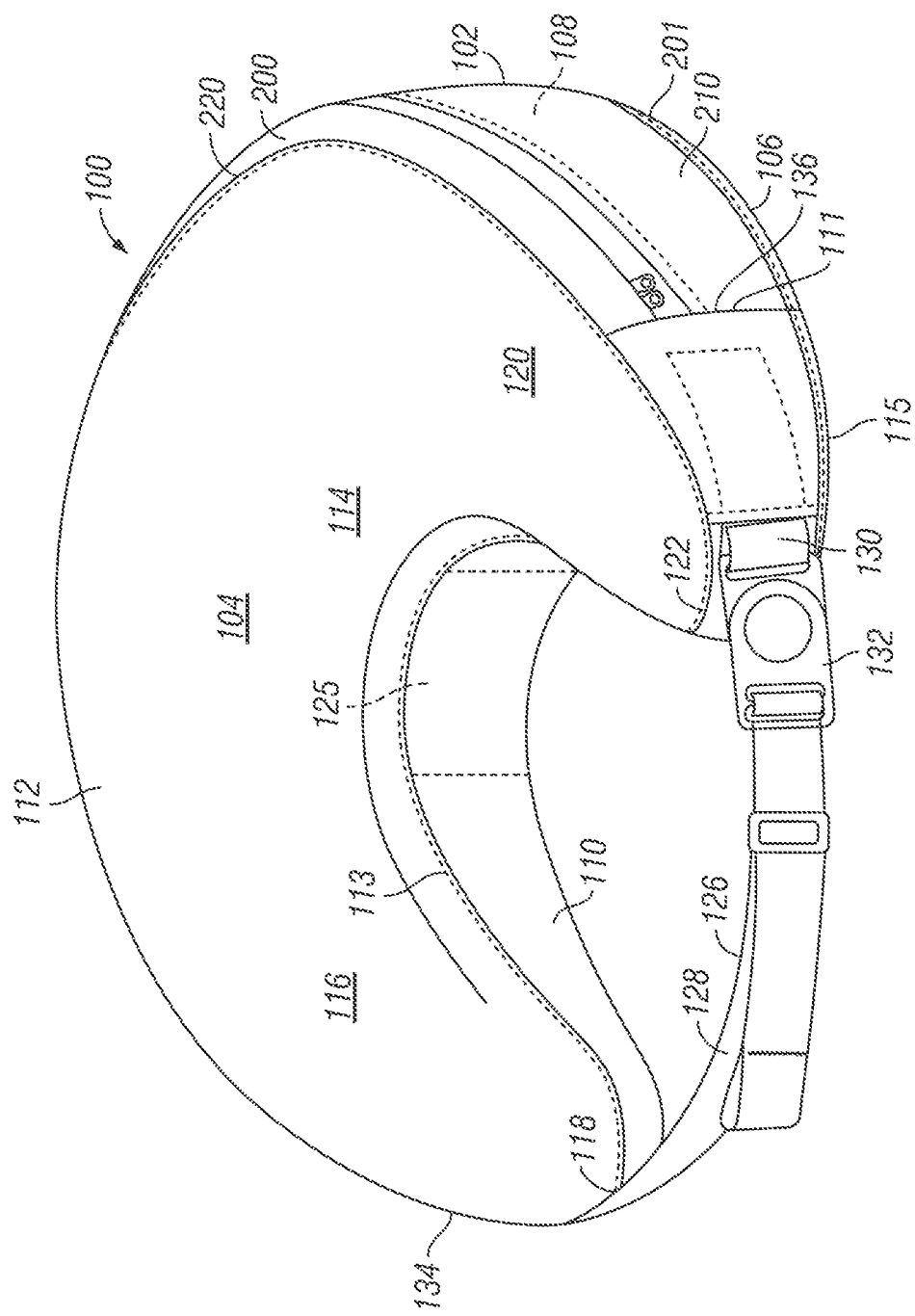
FIG. 1A is a top right perspective view of a nursing pillow according to another embodiment of the invention.
Figure 4:
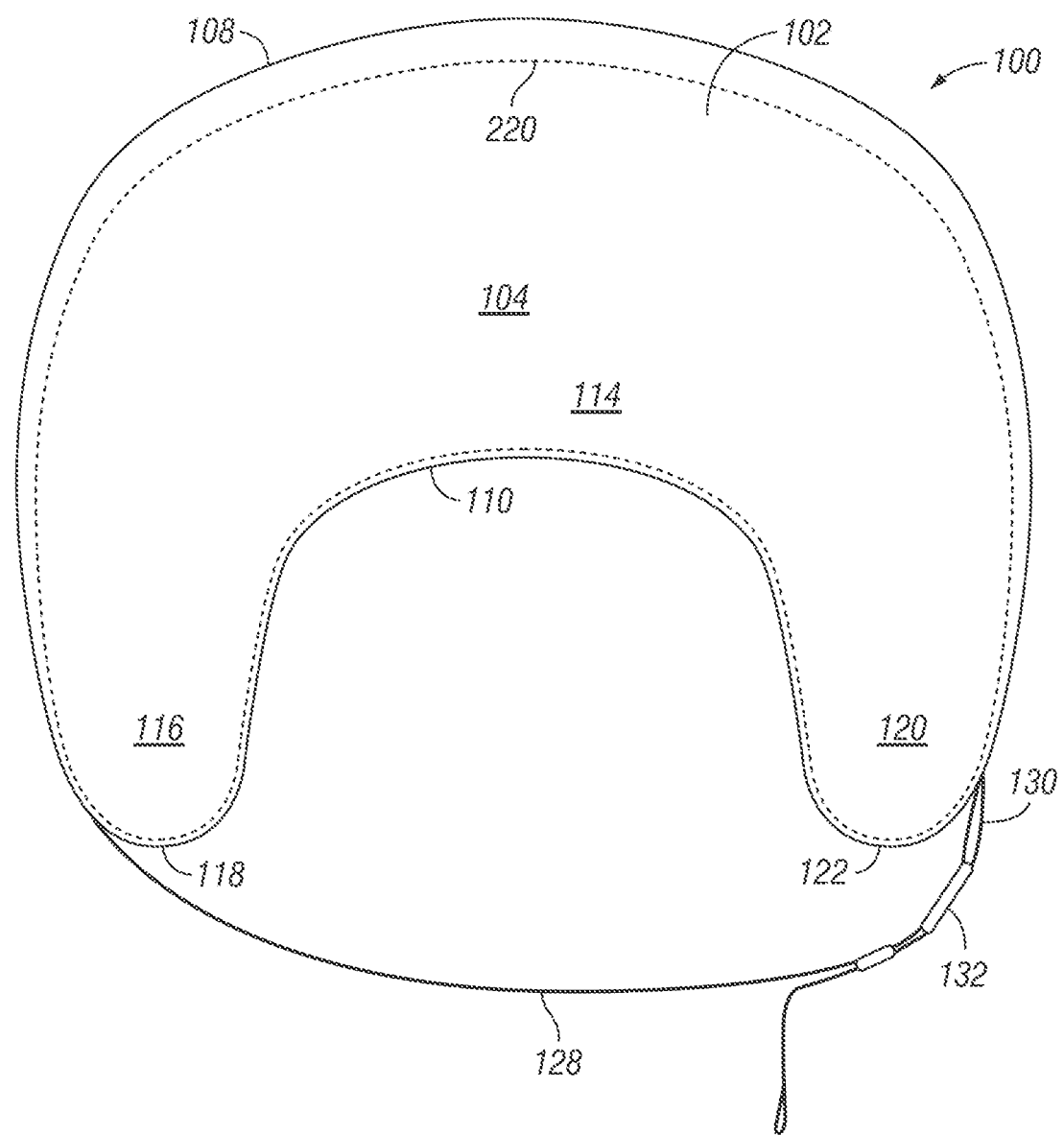
FIG. 4 is a top view of the nursing pillow shown in either FIG. 1 or FIG. 1A.

An alternative placement of a heat therapy pack 125 is shown in dotted line in FIG. 1A. In this embodiment, the heat therapy pack is placed inside the cavity defined by outer shell 102, rearwardly adjacent to the inner panel 110. Further details of thermal therapy packet 125 will be given in conjunction with FIGS. 14A and 14B.

In the illustrated embodiments, a strap 126 is passed around the back of the user to connect the left tip 118 to the right tip 122. The strap 126 may have a left portion 128 and a right portion 130, the distal ends of which may be releasably connected together by a connector 132. In one embodiment, one portion, such as portion 128, intentionally may be much longer than the other portion, such as portion 130, which will position the connector closer to one arm tip than the other one. This position makes it easier for the user to fasten the pillow 100 around her torso. In another embodiment, the strap portions 128, 130 may be of more equal length, so that the connector 132 may be cushioned from contact with the user's back by a cushioned support or back panel 1100 (FIGS. 11-13) The strap 126 may be passed through aback pad 1100, which will be described in more detail below.

The inner panel 110 has a left end 134 that is positioned leftwardly and beyond left arm tip 118. Similarly, the inner panel 110 has a right end 136 that is positioned rightwardly and beyond right arm tip 122.

Figure 5:
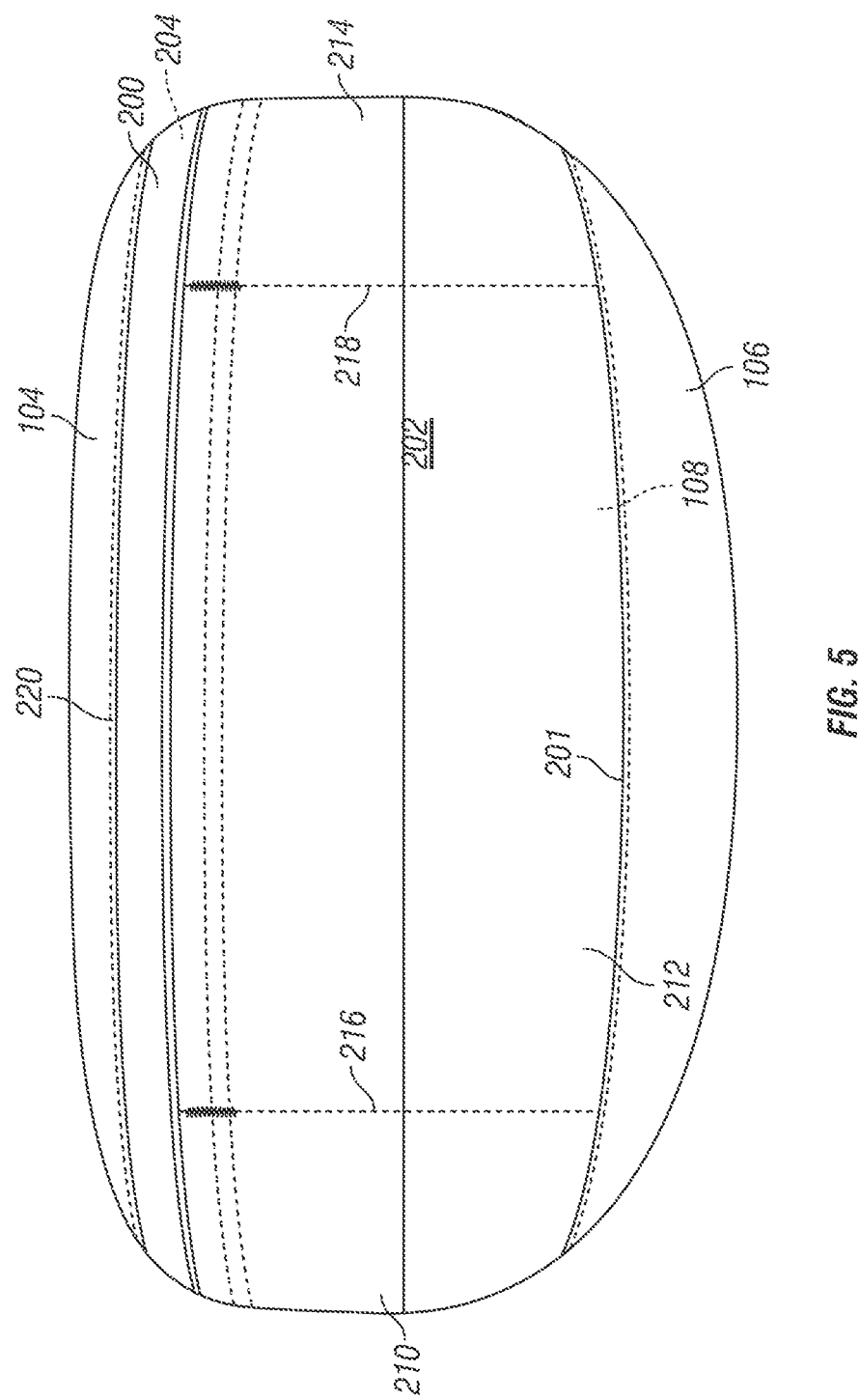
FIG. 5 is a rear or outer devotional view of the nursing pillow shown in either FIG. 1 or FIG. 1A.
Figure 8:
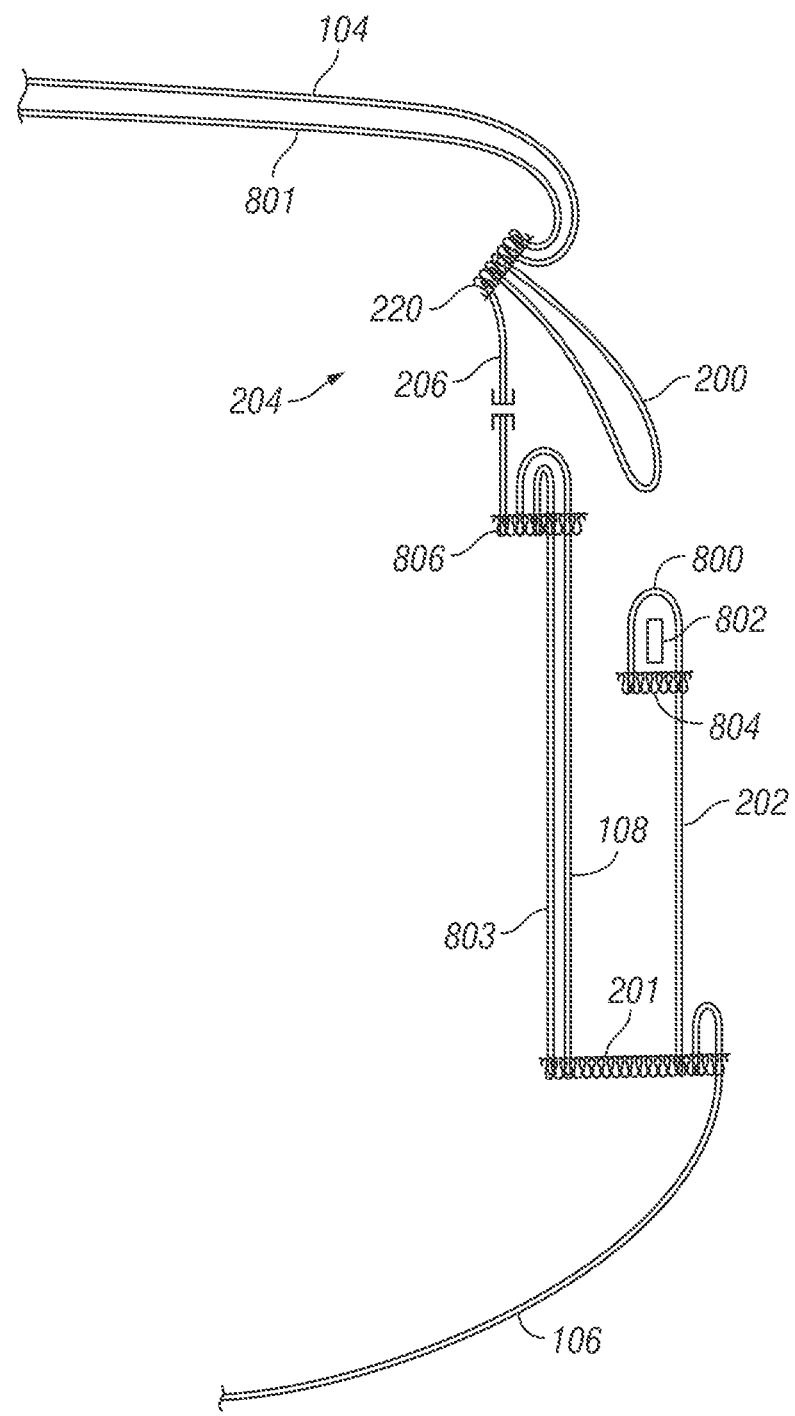
FIG. 8 is a highly schematic sectional view of portions of the top, rear and bottom panels of an outer shell of the nursing pillow, showing details of construction of a rear pocket and zipper opening.

Referring to FIGS. 2, 3 and 5, in the illustrated embodiment, the upper margin of outer panel 108 is joined to the top panel 104 at or near a junction or seam 220 by an opening closure, such as a zipper panel 206 (only the zipper handles are visible here; zipper panel 206 is schematically shown in FIG. 8.) The opening 204 is hidden beneath a zipper draft flap 200, which can be made of a stretchable material and which should not have any nonstretch backing. The opening 204 permits access to the body cavity, so that one or more of the cushionable inserts (described below) may be inserted into or withdrawn from the cavity by the user, and also so that the user may install or remove a heat pack 1500 into or out of the thermal therapy pocket 125 shown in FIG. 1A.

Outer panel 108 may further have one or more pockets which then would form the rear exterior surface of pillow body 112. For example, a right pocket 210 may be formed on a right portion of the outer panel 108, a central pocket 212 may be formed on a rear, central portion of the outer panel 108, and a left pocket 214 may be formed on a left portion of the outer panel 108. As seen in FIG. 5, the pockets 210, 212 and 214 are separated from each other by stitch lines 216 and 218. In the areas where the pockets 210-214 are formed, an extra layer 202 of fabric is stitched to the panel 108. But this extra layer of fabric, which can consist of the same stretchable fabric used to form panels 104-110, 208, 300 more generally is not backed by a nonstretch layer. That nonstretch layer (803, FIG. 8) is disposed only to the interior of the panel 106, which acts as the inner side of the pockets 210-214. Pockets 210-214 may be used to hold accessories such as wipes, formula bottles or toys. In the illustrated embodiments the pocket fabric layer 202 is horizontally coextensive with outer panel 108, and is stitched to the ends of the inner panel 110 at seams 111, 302.

Figure 6:
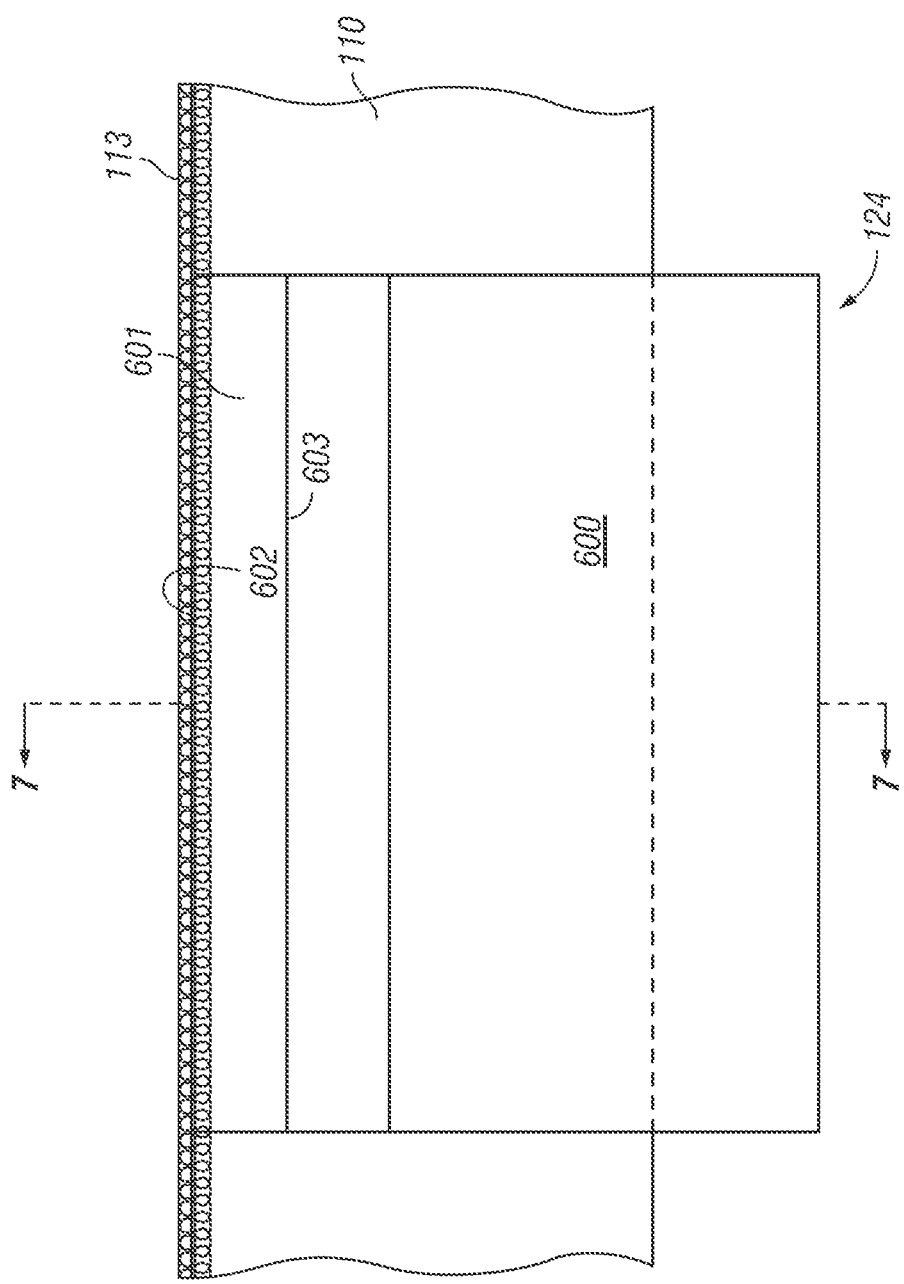
FIG. 6 is a schematic detail of a thermal therapy pocket as joined to an inner panel of the nursing pillow in the embodiment shown in FIG. 1.
Figure 7:
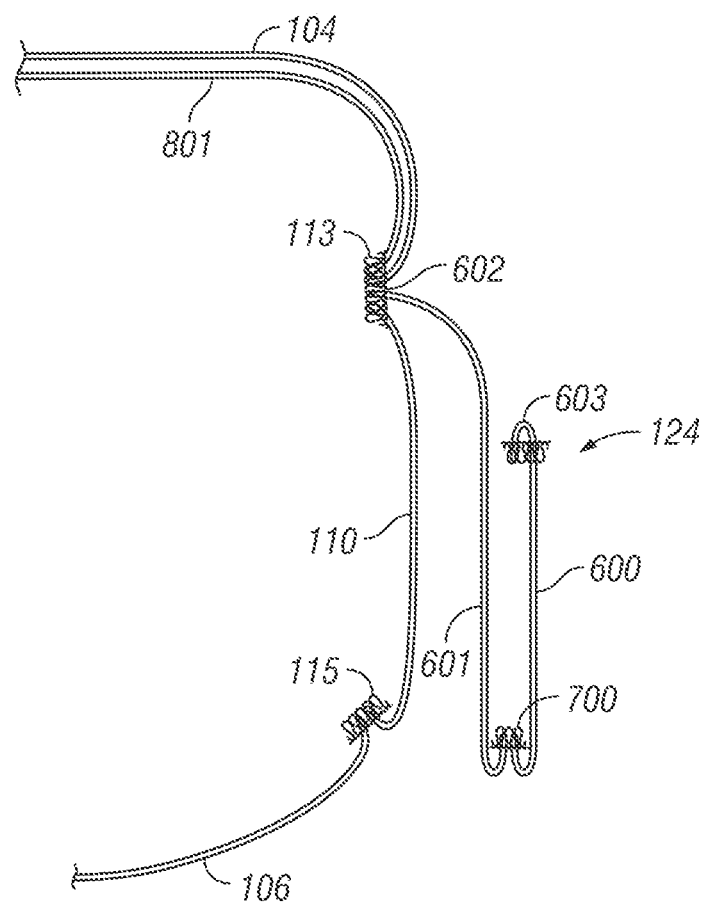
FIG. 7 is a highly schematic cross-sectional view taken substantially along line 7-7 of FIG. 6.

As shown in FIGS. 6 and 7, the thermal therapy pocket 124 may be rectangular in shape when stitched on a flat piece of material that will become inner panel 110; as assembled, the therapy pocket 124 will have a flexible front panel 600 that is vertical but concavely arcuate with respect to the user. Pocket 124 may be formed by a rear panel 601, positioned adjacent inner panel 110 and remote from the user, and a front panel 602, positioned inwardly from panel 601 so as to be adjacent to the user. A top margin 602 of rear panel 601 may be stitched to the seam 113 between inner panel 110 and top panel 104 (FIG. 1). A top margin 603 of the front panel 600 may be positioned about 2 cm below top margin 602. A top portion of panel 600 may be folded over and stitched to create top margin 603, and so as to lend reinforcement to the top margin 602. The panels 600, 601 may be formed of the same material forming inner panel 110, such as a stretchable polyester/spandex blend. Bottom ends of pocket panels 600, 601 may be joined at a seam 700.

In the illustrated embodiment, the height of pocket 124 is about 13.5 cm. This means that in use, a portion of the pocket 124 may extend below the lower margin of inner panel 110. As enclosing a heat pack 1500 of appreciable thickness, the pocket 124 may not extend below inner panel 110 by so much, if at all.

FIGS. 7, 8, 13, 14A and 14B are highly schematic not least because they show, for the purpose of clarity adjacent fabric layers spaced from each other. In actuality, the panels making up the outer shell 102 and pockets joined thereto will be tightly stretched over the cushionable insert(s) filling up the interior and will be adjacent to each other.

Figure 14A:
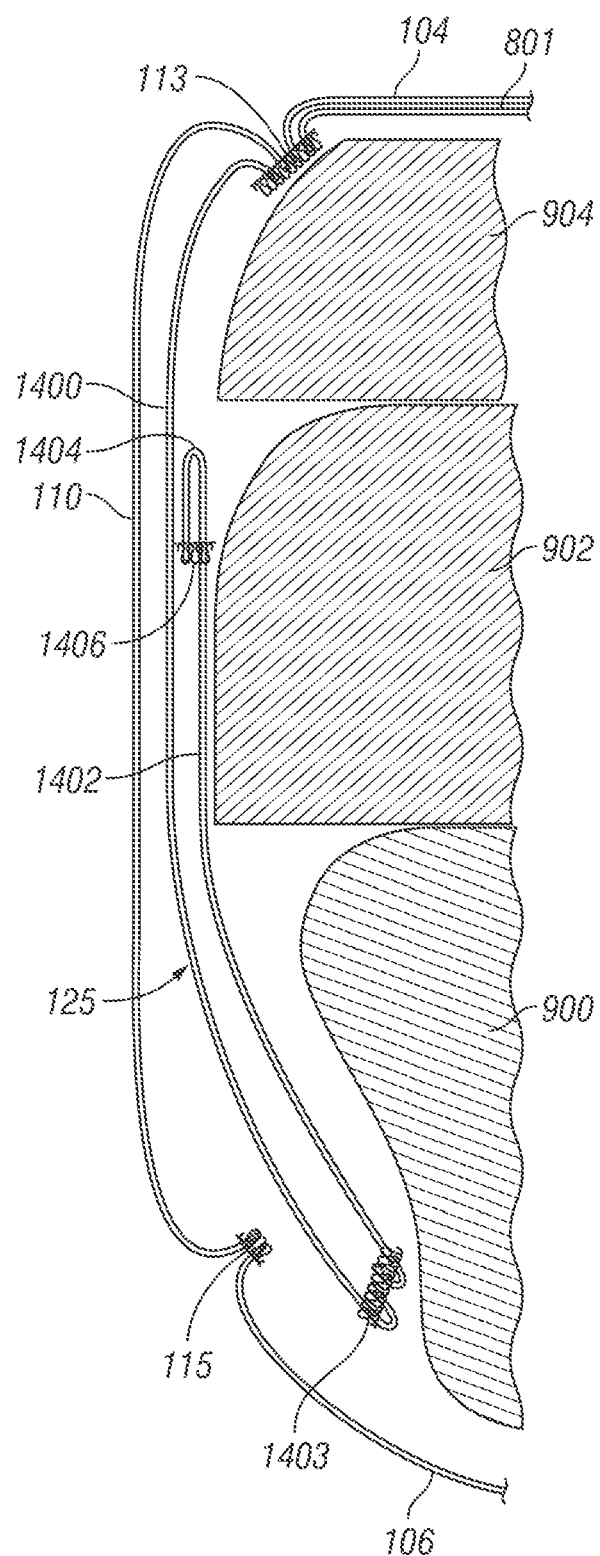
FIG. 14A is a highly schematic sagittal sectional view of a front portion of the nursing pillow shown in FIG. 1A, without a thermal therapy pack having been installed.
Figure 14B:
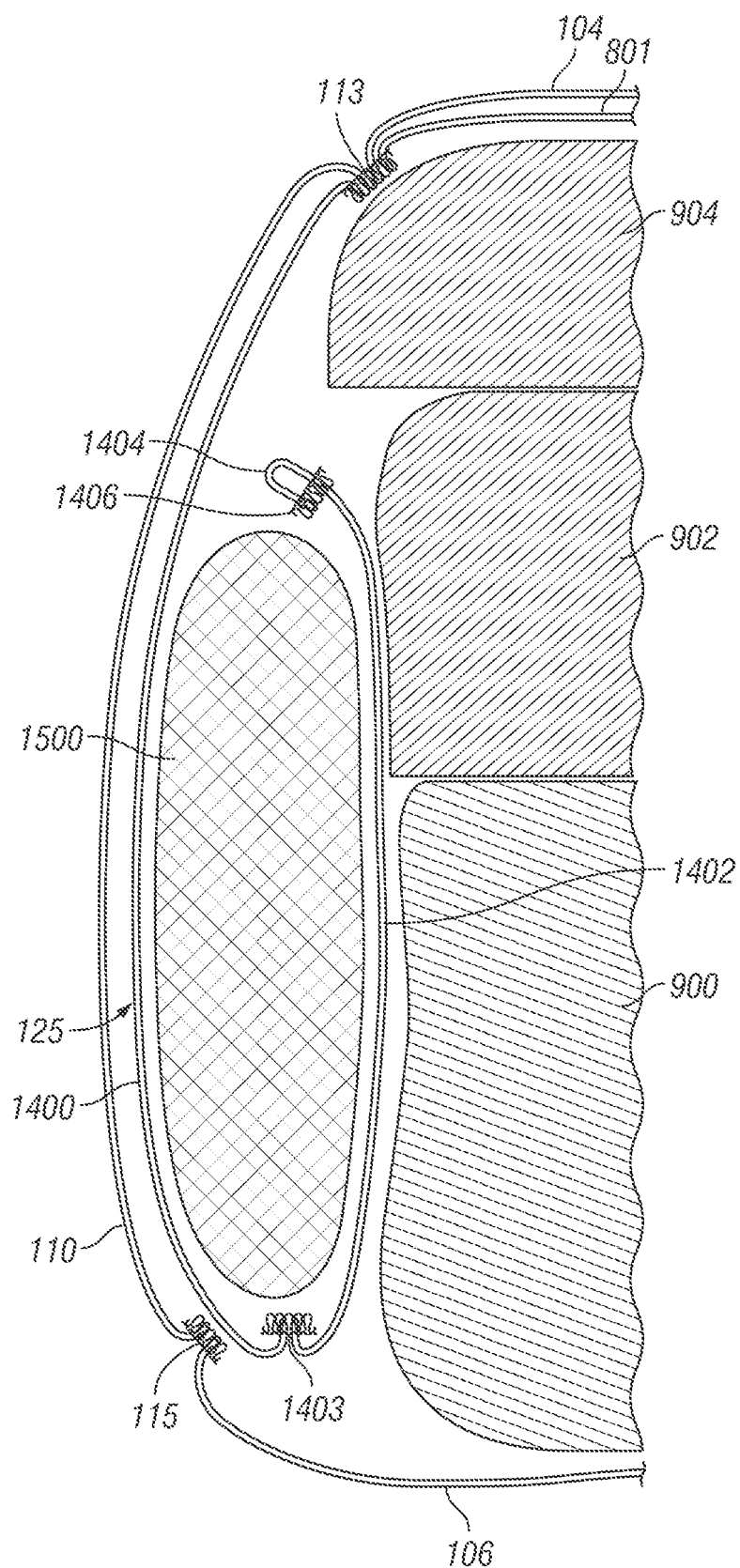
FIG. 14B is a view similar to FIG. 14A, with a thermal therapy pack having been installed.

FIGS. 14A and 14B show the disposition and use of a thermal therapy pocket 125, located to the interior of inner panel 110 to be in the cavity defined by outer shell 102. Pocket 125 may be constructed of the same material used to make up pocket 124. A top end of an inner pocket panel 1400 is stitched at seam 113 to inner panel 110, top panel 104 and top backing layer 801. Without containing a heat pack 1500 or the like, the inner pocket panel 1400 will downwardly extend beyond outer shell seam 115. A bottom end of an outer pocket panel 1402 is stitched at seam 1403 to the bottom end of panel 1400. Pocket panel 1402 upwardly extends along panel 1400 to panel 1402's upper end 1404, where the material is folded back and stitched to itself it a seam 1406.

To get access to time pocket 125, zipper panel 206 is unzipped, and the top panel 104 and backing layer 801 are peeled toward the front. The user then inserts a heat pack 1500 into the pocket 125 from above, or withdraws pack 1500 from pocket 125. As holding a heat pack 1500, the walls 1400, 1402 bulge outward, so the height of pocket 125 decreases (FIG. 14B). The presence of heat pack 1500 inside the pillow cavity will have a tendency to distort the flexible structures around it to various degrees. Stretchy panels 1400 and 110 will bulge frontward somewhat; stretchy pocket panel 1402 will be displaced rearward. Top end 1404 will have more resistance to displacement, as it has been reinforced by an extra layer of material. This will have a tendency to keep pocket 125 closed and the heat pack 1500 contained. The front ends of relatively firm polyurethane foam inserts 902 and 904 will be displaced a little, and the front end of the relatively soft, poly-filled insert 900 will be rearwardly displaced by a larger amount.

As seen in the highly schematic FIG. 8, a top edge 800 of the external panel 202 making up pockets 212-214 may be formed by folding over and stitching a top portion of the panel 202 to itself at seam 804. As so joined, the panel 202 may contain a band 802 of elastic material which increases the resistance of the pocket edge to stretching, and which enhances its ability to close the pocket(s) 212-214 and more securely hold any contents. A bottom edge of pocket panel 202 is joined at seam 201 to outer panel 108, nonstretch backing 803 and bottom panel 106. Top ends of panel 108 and nonstretch backing 803 are joined at a seam 806 to the zipper panel 206. Ends of top panel 104, nonstretch backing layer 801 and zipper flap 200 are joined by seam 220.

Figure 9:
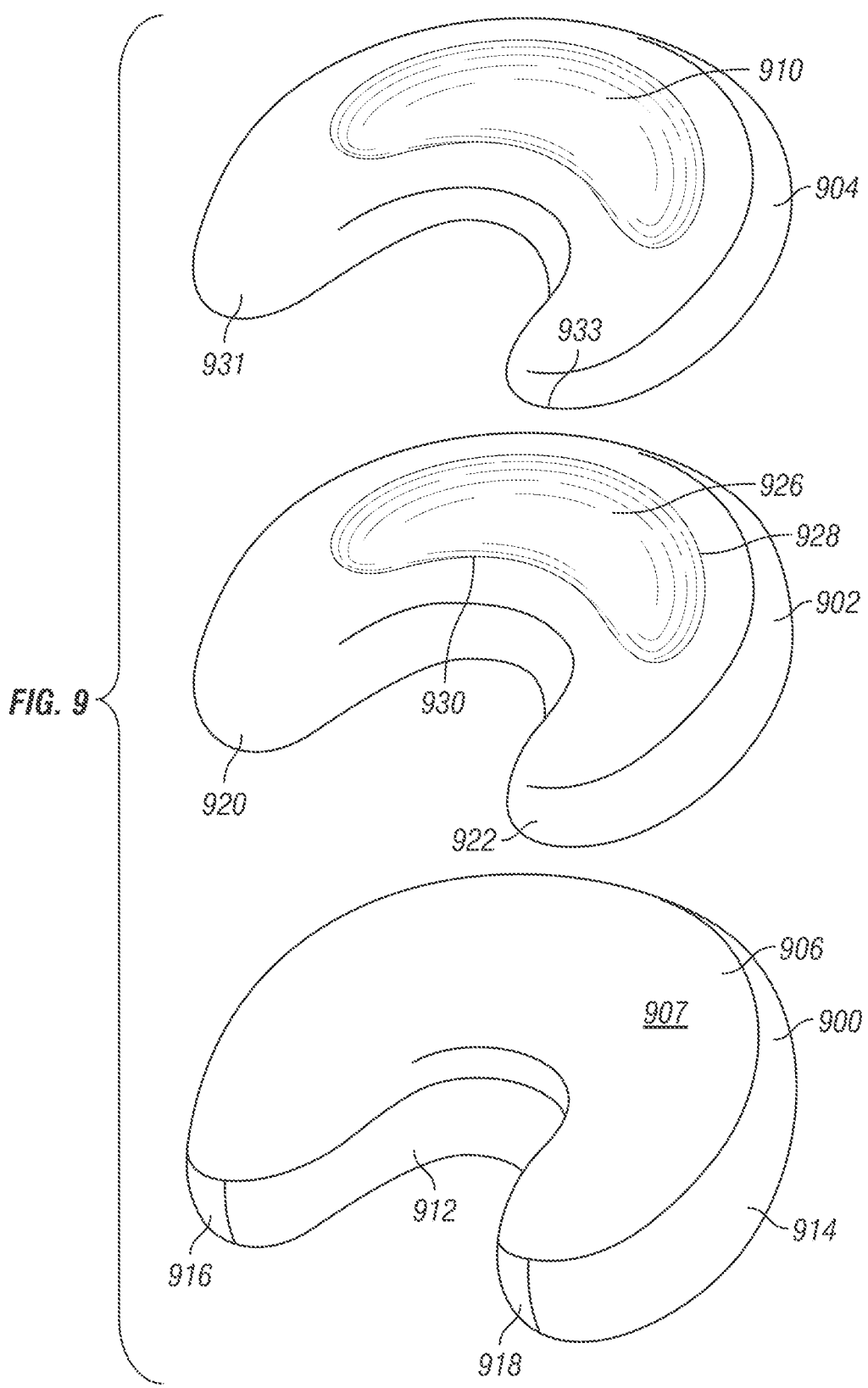
FIG. 9 is an exploded view of first, second and third inserts for selective placement in the outer shell of the nursing pillow.
Figure 10:
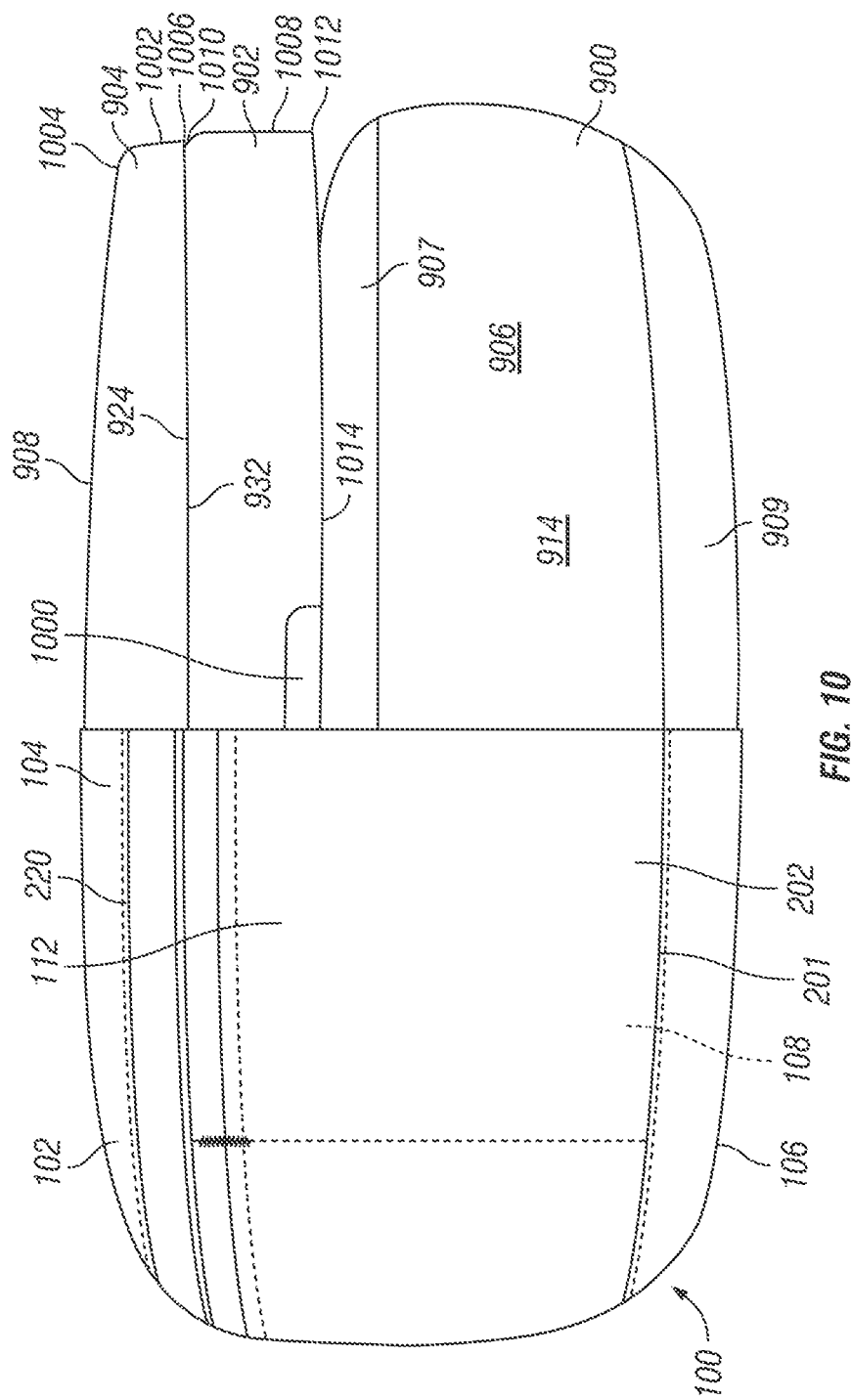
FIG. 10 is a rear devotional view, with the outer shell partially removed, showing the arrangement of the first, second and third insets inside of the outer shell when all three inserts are used.

As seen in FIGS. 9 and 10, the cushionable inserts provided with the nursing pillow include a first, bottom insert 900, a second, middle insert 902, and a third, top insert 904. Each of inserts 900-904 will occupy the middle portion 114 and left and right arms 116, 120 of the pillow body 112 and are substantially coextensive in plan view. Inserts 900-904 however, can have different degrees of cushionability or firmness. The first insert 900 is the least film of the three, and may be constituted by an inner shell 906 filled with a fill which could comprise polyester fill. This insert is meant to be disposed adjacent to and somewhat conform to the lap or legs of the user. Inner shell 906 may in turn be composed of a top panel 907, a bottom panel 909, an inner panel 912 that joins top panel 907 to bottom panel 909 at the concavely arcuate front of the insert, and an outer panel 914 that with panel 912 forms a continuous peripheral band, and which joins top panel 907 to bottom panel 909 at the convexly arcuate, rear of insert 900. The inner shell 906 may be formed of panels of a nonstretch fabric such as 100% cotton in an uncompressed state, insert 900 may be about 18 cm high at its greatest extent. The thickness of insert 900 gradually decreases as one approaches the ends 916, 918 of its arms.

The second insert 902 may be constituted by an elastomeric foam and will be firmer than insert 900. Insert 902 may, for example, be constituted by a medium-density polyurethane foam, and more particularly by one having a density of 50 Kpa and an indention load deflection (ILD) of 70. The second insert 902 may have a thickness at its greatest extent of about 5 cm. The thickness of second insert 902 gradually decreases as one approaches the end 920 of a left arm thereof, and also as one approaches the end 922 of a right arm thereof. At ends 920, 922, the thickness of insert 902 may be about 1.6 cm.

A top surface 924 of the insert 902 has formed therein a bean-shaped depression 926, sized to receive the body of an infant when third insert 904 is not being used. The depression 926 may have a length at its greatest extent of about 24-27 cm, and a front-to-rear width of about 10-14 cm. A depth of the depression may be about 1 cm. An outer edge 926 is convexly curved white an inner edge 930 of the depression 925 is concavely curved, with a length of the outer edge 928 being greater than a length of the inner edge 930. In general, the edges 928, 930 of the depression 926 are roughly concentric with the arcs made by outer panel 108 and inner panel 110.

The third insert 904 may be constituted by an elastomeric foam that may have the same firmness as that of the second insert 902, or one that has a higher firmness. Insert 904 may be constituted by a polyurethane foam. Insert 904 is thinner than insert 902, and can have a greatest thickness of about 2.8 to 3 cm, tapering down to a thickness at its arm ends 931, 933 of about 1 cm. In one embodiment, the slope, of the top surface 908 of insert 904 relative to the bottom surface 932 thereof is not as dramatic as the slope between the top surface 924 of insert 902 relative to the bottom surface thereof. This difference in slopes is made so that, in those instances in which both inserts 902 and 904 are used, the summation of the slopes of stacked inserts 902 and 904 is not too much.

A top surface 908 of the third insert 904 has formed therein an elongate, bean-shaped depression or trough 910. Like depression 926, the depression 910 is sized to receive the torso and head of a nursing infant. The depression is oriented to be transverse to the user, so that the nursing infant will lay across the torso of the user rather than on a radius from the riser. The depression 910 may have a depth at its greatest extent of about 1 cm. The shape and dimensions of depression 910 may be similar to the shape and dimensions of second insert depression 926. On the other hand, the dimensions of depression 910 may be chosen to be somewhat smaller than the dimensions of depression 926 as the nursing infant received thereon may be significantly smaller in size than that of an infant received on depression 926; as using only inserts 900 and 902, it is contemplated that the nursing infant received thereon will be older and larger than a younger infant received on a stack of inserts 900, 902 and 904.

Figure 9A:
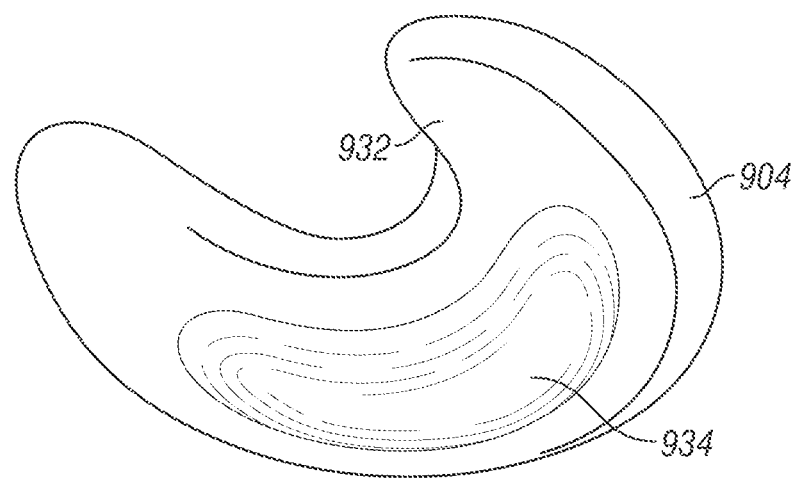
FIG. 9A is a bottom perspective view of a third insert according to one embodiment of the invention.

As seen in FIG. 9A, a bottom surface 932 of the insert 904 has an eminence or bump 934 that is the complement in size and shape of depression 926. When insert 904 is used, the hump 934 will mate with the depression 926 in insert 902, removing any gap that may otherwise occur in the supporting foam and providing resistance to the lateral displacement of insert 904 relative to insert 902.

Returning to FIGS. 1, 2 and 3, in use, the bottom panel 106 of outer shell 102 will contact the user's legs and as such will be oriented to be horizontal, or slightly downwardly and outwardly slanted. In this orientation, the top panel 104 will substantially occupy a plane that is downwardly inclined, from rear to front, toward the torso of the user. This will create a tendency for the infant to remain close to the torso of the user and will further reduce the danger of the infant rolling off.

FIG. 10 is a back devotional view in which the outer shell 102 has been removed from haft of the body 112. In the configuration shown in FIG. 10, all three inserts 900, 902 and 904 are being used, and are stuffed under compression into the cavity defined by the outer shell 102. The second insert 902 may have a cutout 1000 formed in its rear surface sized to receive the user's fingers of one hand, to aid in pulling out or inserting the middle insert 902. A similar cutout (not shown) could be formed at the rear edge of the third insert 904.

In those embodiments where inserts 902 and 904 are polyurethane or other moldable foam, it is possible to mold them so that their top profiles and their bottom profiles intentionally do not match. Hence, as illustrated in FIG. 10, top insert 904 has a somewhat sloped side 1002. Side 1002 makes a rounded corner 1004 with top insert surface 908, but makes a sharp corner 1006 with bottom surface 932. Similarity a somewhat sloped side 1008 of middle insert 902 makes a rounded corner 1010 with top surface 924 of middle insert 902, but makes a sharp corner 1012 with the bottom surface 1014 of middle insert 902. This is done because in use, the outer shell 102 is tautly stretched over such of inserts 900-904 the user has chosen to use. Where all three inserts 900-904 are used, the rounded corner 1004 will make a top rounded corner of the entire pillow 100. When only two inserts 900, 902 are used, rounded corner 1006 will make a top rounded corner of the entire pillow 100. But the sharp corners 1006, 1012 aid in keeping the fabric sidewall straight, and in reducing any dimple in the outer shell 102 which might otherwise occur.

In operation, the user can freely select which of the inserts 900-904 should constitute the pillow body 112. Bottom insert 900, disposed adjacent the user's legs, will usually be selected to make up all or a part of the pillow body. For newborn infants, all three inserts 900, 902 and 904 can be used. When all three inserts are used, the vertical separation of the infant from the user's legs is at its maximum. As the baby grows, the amount of elevation needed may decrease. In another configuration, only inserts 900 and 902 would be used, and, to accommodate further growth of the baby, the user may use a combination of inserts 900 and 904. If the user's torso is short, the user may only select two of the inserts for use, even for newborns. For older infants, the user may use only insert 900.

Figure 11:
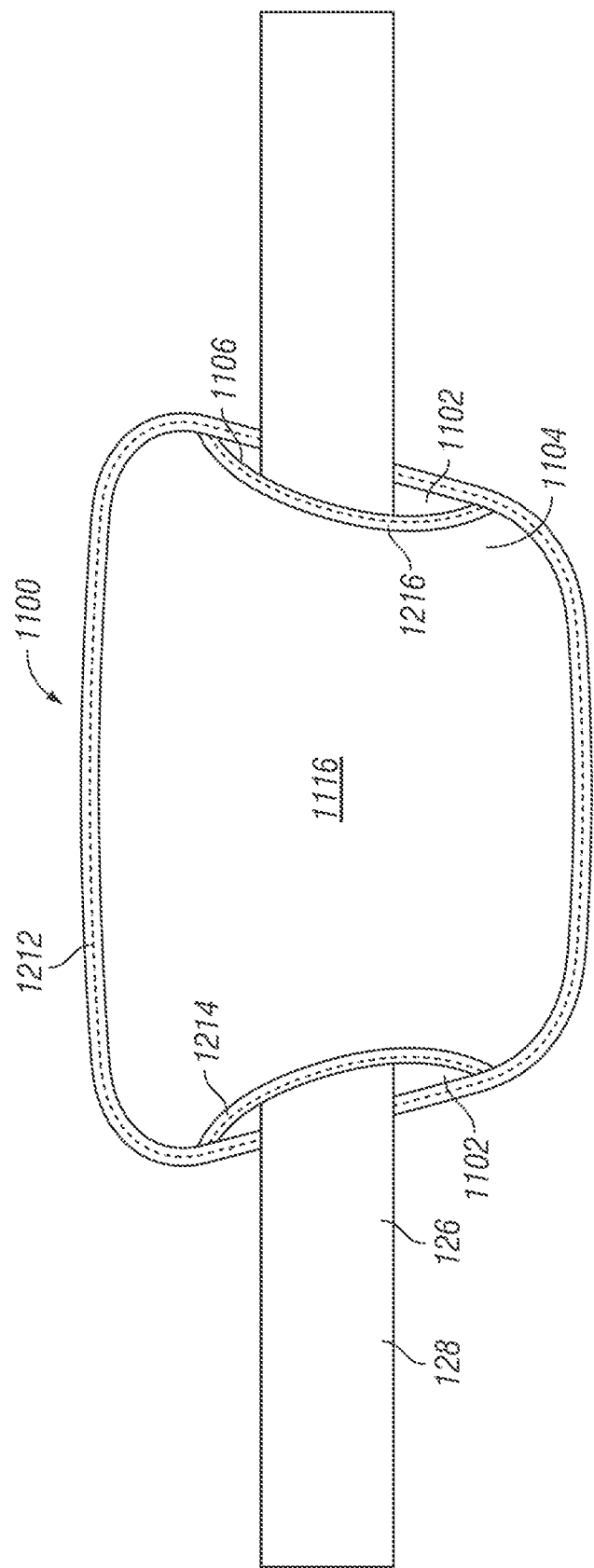
FIG. 11 is an exterior devotional view of a back panel for use with the invention, shown with an arm-connecting strap inserted through a passageway thereof.
Figure 12:
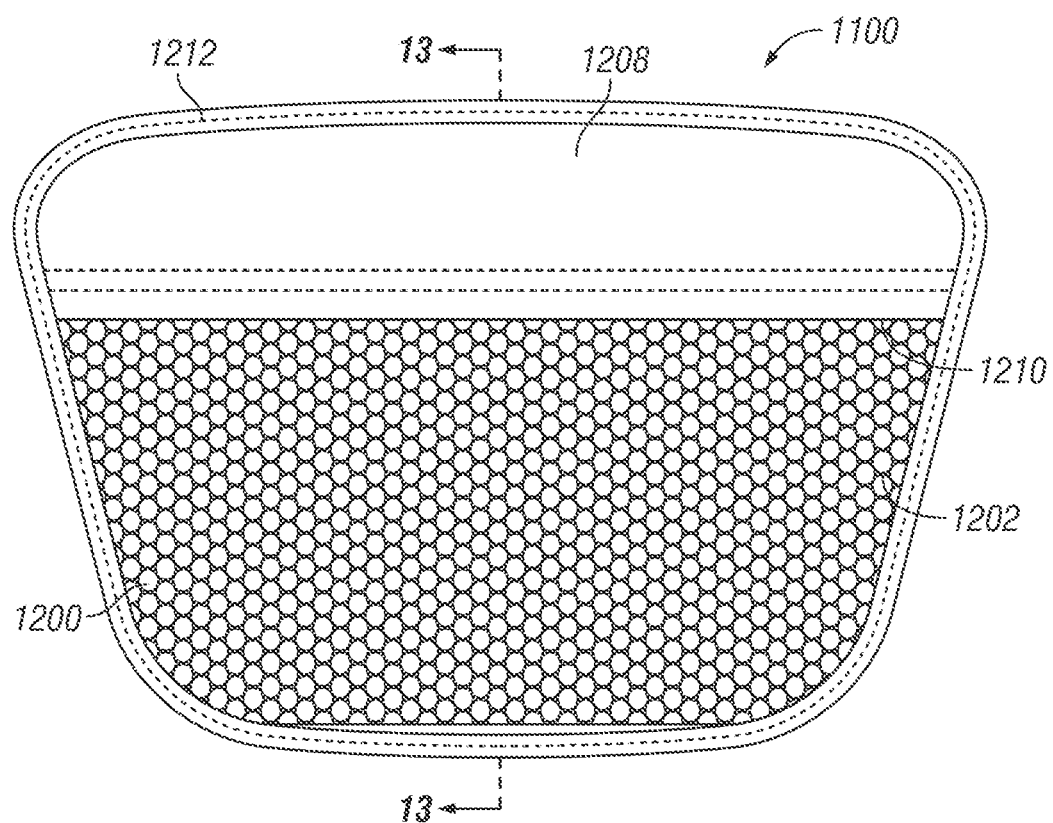
FIG. 12 is an interior elevational view of the back panel shown in FIG. 11.
Figure 13:
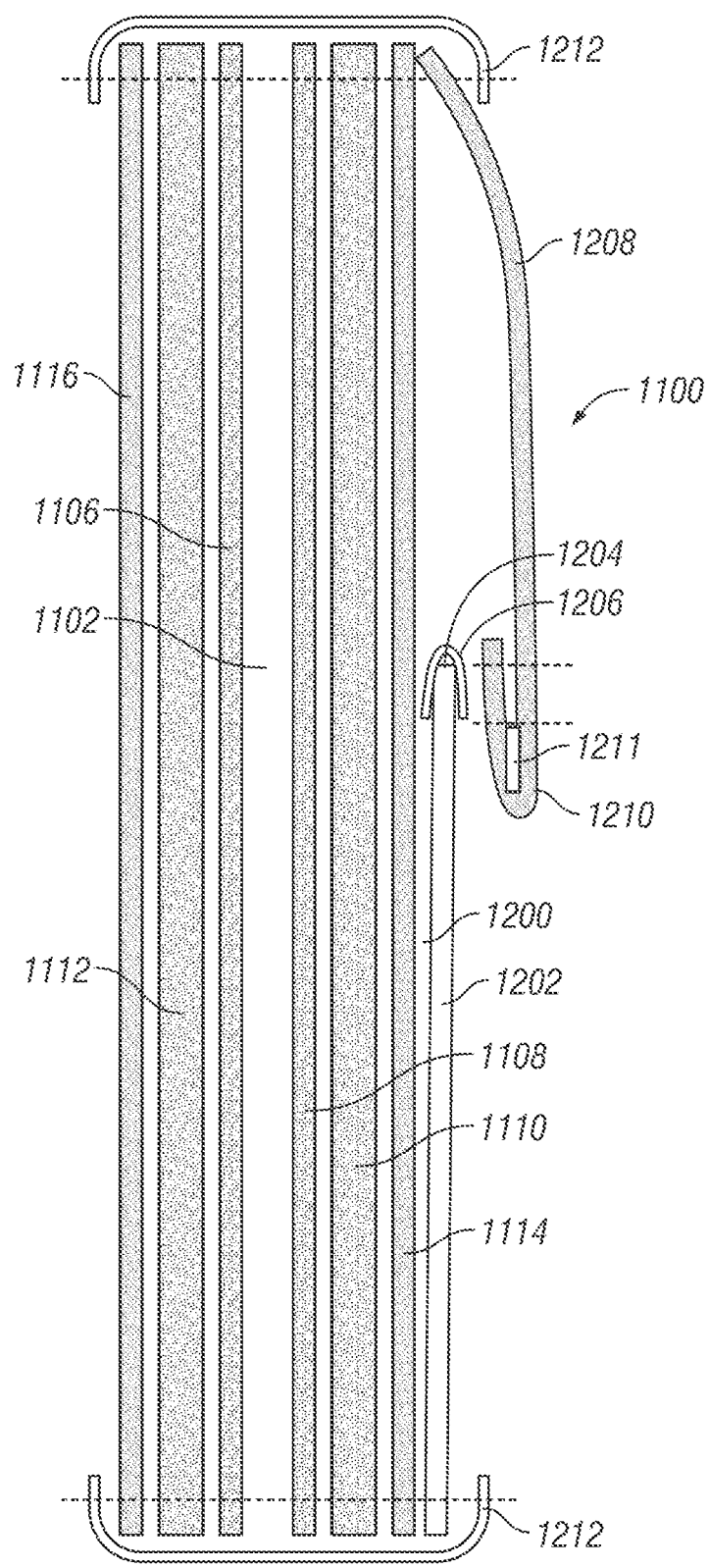
FIG. 13 is a highly schematic sectional view taken substantially along line 13-13 of FIG. 12, showing the construction of the back panel.

The nursing pillow may be used with a padded back support or panel, an embodiment of which is seen at 1100 in FIGS. 11-13. The panel 1100 is provided to distribute the force applied by connecting strap 126 to a larger area of the user's back. In FIG. 11, the strap 126 can be seen passing through a hole or passageway 1102, and in between a back portion 1104 and a front portion 1106 of the support 1100.

A preferred overall construction of the back panel 1100 is schematically represented in FIG. 13. The through-hole or strap passage 1102 is flanked and defined on the outside by a fabric layer 1106 and on the inside by another fabric layer 1108. Fabric layers 1106 and 1108 can be identical in construction and can be constituted by 300D nylon fabric, for example.

Disposed to the inside of layer 1108 is a foam layer 1110. Foam layer 1110 may be made of polyurethane foam and may be about 2 to about 3 mm thick. Similarly, a foam layer 1112 is disposed to the exterior of layer 1106. This layer 1112 can also by about 2 to 3 mm thick and be of the same composition as foam layer 1110. A general interior surface of back panel 1100 is formed by fabric layer 1114, which may be formed of a stretchable fabric such as polyester/spandex and which can match in composition the fabric making up the exterior surface of all of the panels 104—110, 208, 300 of outer shell 102. An exterior surface of back panel 1100 is formed by fabric layer 1116, which can match in composition the interior surface layer 1114.

Optionally, the back panel 1100 may have an interior-facing pocket 1200, as seen in FIGS. 12 and 13. This pocket 1200 is sized to receive a thermal therapy pack such as heat pack 1500, and is provided to relieve possible back pain of the nursing mother. In one embodiment, two such heat packs 1500 are provided, so that one of them may be inserted into pocket 1200, and the other inserted into pocket 124 or 125. The pocket 1200 is formed by interior fabric layer 1114, on its outer side, and by a mesh layer 1202, on its inner side. A top edge 1204 of the mesh layer 1202 is bound by a binding layer 1206. The pocket 1200 further has a top flap 1208 with a bottom edge 1210 that is folded over and stitched, as shown. There can be, for example, a 15 mm overlap between top edge 1204 of the pocket and bottom edge 1210 of the flap. The top flap 1208 may be composed of the same material making up the exterior surface of outer shell 102, such as a stretchable polyester/spandex. As folded over and stitched, the bottom edge 1210 encases an elastic band 1211. Band 1211 will permit the user to open flap 1208 to insert an article (such as a heat pack 1500) into the pocket 1200, but will otherwise act to increase, tensile force when the flap is opened, and will more quickly return the flap 1208 to the closed position shown.

A binding layer 1212 is used to stitch the various layers 1106, 1108, 1110, 1112, 1114, 1116 and 1202 together. The binding layer extends around the ends of layers 1106, 1108, 1110, 1112, 1114, 1116 and 1202 and, as seen in FIGS. 11 and 12, forms the lateral periphery of the back panel 1100. Further binding layers 1214 and 1216 (FIG. 11) bind together lateral edges of layers 1106, 1112 and 1116, and help protect these lateral edges of the hole 1102 through which strap 126 is threaded.

In summary, a novel nursing pillow has been illustrated and described that has first, second and third inserts, with the second and third inserts being of a firmness greater than that of the first insert, and where the inserts are individually selectable by the user for use in supporting the nursing infant. A thermal therapy pocket is disposed on an internal panel so as to permit a heat or cold pack to deliver heat or cold to the torso of the user. A back support may have a similar pocket to contain a thermal therapy pocket for the user's back.

While illustrated embodiments of the present invention have been described and illustrated in the appended drawings, the present invention is not limited thereto but only by the scope and spirit of the appended claims.

We claim:

1. A nursing pillow comprising:
a flexible outer shell surrounding a pillow body, the body having a cavity formed therein, an opening formed in the outer shell to provide access to the cavity;
a plurality of inserts each capable of being inserted through the opening into the cavity to be disposed in the cavity, the inserts including first and second inserts, ones of the first and second inserts being selectable by the user to be disposed inside of the cavity, wherein in a first configuration of the nursing pillow, both of the first and second inserts are selected by the user to be disposed inside of the cavity, the second insert then being positioned above the first insert so that the first and second inserts are arranged in layers;
the outer shell having a top surface for receiving a nursing infant, the first insert having a top surface, the nursing pillow being usable in a second configuration in which the top surface of the first insert is adjacent the top surface of the outer shell, an elongate concave depression formed in the top surface of the first insert for receiving the nursing infant and
the second insert having a bottom surface which, when both the first and second inserts are used in the first configuration of the nursing pillow, faces the top surface of the first insert, a convex bump on the bottom surface of the second insert fitting into the concave depression on the top surface of the first insert.

2. The nursing pillow of claim 1, wherein the first and second inserts are made of elastomeric foams having different firmnesses.

3. The nursing pillow of claim 1, wherein the first and second inserts are made of an elastomeric foam having a same firmness.

4. The nursing pillow of claim 1, wherein the plurality of inserts further includes a third insert selectable by the user to be disposed inside of the cavity, and wherein when the user selects the third insert and at least one of the first and second inserts to be disposed inside of the cavity, the third insert will be disposed below the at least one of the first and second inserts.

5. The nursing pillow of claim 1, wherein the second insert has a top surface, an elongate concave depression formed in the top surface of the second insert.

6. The nursing pillow of claim 1, wherein the elongate concave depression is bean-shaped.

7. A nursing pillow comprising:
a flexible outer shell enclosing a body, the body having a cavity therein, the outer shell having a top panel defining a top surface of the body, a bottom panel defining a bottom surface of the body, and an inner panel joining the top panel to the bottom panel, the inner panel having a substantially vertical surface for disposal adjacent a torso of a user, the user being a nursing mother or other caregiver;
at least one insert disposed in the cavity and being resiliently yieldable responsive to a downward force placed on the top surface of the body;
a thermal therapy pocket vertically disposed so as to face the torso of the user, a rear panel of the thermal therapy pocket disposed remote from the user and proximate to the inner panel of the outer shell, a top margin of the rear panel of the thermal therapy pocket joined to the inner panel of the outer shell, the rear panel of the thermal therapy pocket having a bottom margin, a front panel of the thermal therapy pocket disposed proximate to the user and remote from the inner panel of the outer shell, a bottom \margin of the front panel of the thermal therapy pocket joined to the bottom margin of the rear panel of the thermal therapy pocket; and
a heat or cold therapy device adapted to be received in the thermal therapy pocket.

8. The nursing pillow of claim 7, wherein the body has a middle portion extending outwardly from the inner panel, a left arm extending leftwardly around the torso of the user from the middle section and a right arm extending rightwardly around the torso of the user from the middle section, each of the left and right arms having a tip, a left end of the inner panel disposed leftward of the tip of the left arm, a right end of the inner panel disposed rightward of the tip of the right arm, the inner panel being formed of a stretchable material.

9. The nursing pillow of claim 8, wherein the outer shell further has an outer panel joining the top panel to the bottom panel, the outer panel having a left end and a right end, the left end of the outer panel joined to the left end of the inner panel, the right end of the outer panel joined to the right end of the inner panel, the top panel and outer panel each being backed with non-stretch interfacing such that the nursing pillow retains its overall shape.

10. The nursing pillow of claim 7, further comprising at least one pocket disposed on the outer panel, a pocket panel disposed exteriorly of the outer panel to form an outer surface of said at least one pocket, the pocket panel formed of a stretchable material.

11. The nursing pillow of claim 7, wherein an opening to the cavity is formed near a junction of the outer panel and the top panel, a draft flap disposed exteriorly of the outer panel to cover the opening, the draft flap formed of a stretchable material.

\* \* \* \* \*